United States Patent [19]

Mullin, Jr. et al.

[11] Patent Number: 4,632,925
[45] Date of Patent: Dec. 30, 1986

[54] N-SUBSTITUTED DIPHENYLPIPERIDINES AND ANTIOBESITY USE THEREOF

[75] Inventors: John G. Mullin, Jr., Hawthorne; Richard W. Kierstead, North Caldwell; Joseph Triscari, Bloomfield, all of N.J.

[73] Assignee: Hoffmann-La Roche Inc., Nutley, N.J.

[21] Appl. No.: 785,113

[22] Filed: Oct. 7, 1985

[51] Int. Cl.$^4$ ............... A61K 31/505; A61K 31/445; C07D 211/68; C07D 239/02
[52] U.S. Cl. ..................................... 514/256; 546/194; 546/210; 514/318; 514/326; 544/335; 544/242
[58] Field of Search ............... 546/194, 210; 514/256, 514/318, 326; 544/335, 242

[56] References Cited

U.S. PATENT DOCUMENTS 4,076,717 2/1978 Kreider ............................... 546/194

Primary Examiner—Henry R. Jiles
Assistant Examiner—Robert C. Whittenbaugh
Attorney, Agent, or Firm—Jon S. Saxe; Bernard S. Leon; William G. Isgro

[57] ABSTRACT

Compounds of the formula

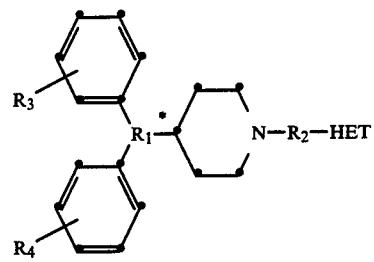

wherein $R_1$ is

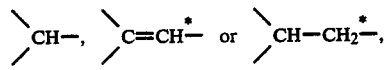

the asterisk denotes the specific bonding orientation to the piperidine moiety; $R_2$ is alkylene or $-CO-(CH_2)_n-$ wherein n is 0 to 11; $R_3$ and $R_4$, independently, are hydrogen, halogen or lower alkoxy; and HET is pyridinyl, pyrimidinyl or imidazolyl, and salts thereof with pharmaceutically acceptable acids, are described. The compounds of formula I exhibit insulin lowering activity and are useful as antiobesity agents.

20 Claims, No Drawings

N-SUBSTITUTED DIPHENYLPIPERIDINES AND ANTIOBESITY USE THEREOF

BRIEF SUMMARY OF THE INVENTION

The invention relates to N-substituted diphenylpiperidines of the formula

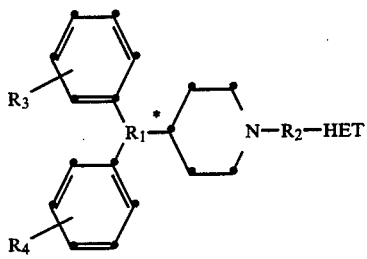

wherein $R_1$ is

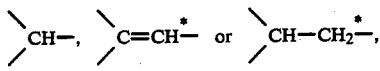

the asterisk denotes the bonding orientation to the piperidine moiety; $R_2$ is alkylene or $-CO-(CH_2)_n-$ wherein n is 0 to 11 carbon atoms, preferably from 3 to 9 carbon atoms; $R_3$ and $R_4$, independently, are hydrogen, halogen or lower alkoxy; and HET is pyridinyl, pyrimidinyl or imidazolyl, and salts thereof with pharmaceutically acceptable acids. The compounds of formula I exhibit insulin lowering activity and are therefore useful as antiobesity agents.

DETAILED DESCRIPTION OF THE INVENTION

The invention relates to N-substituted diphenylpiperidines of the formula

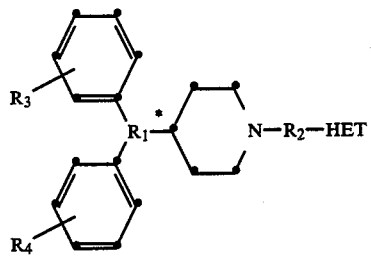

wherein $R_1$ is

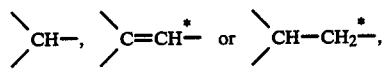

the asterisk denotes the bonding orientation to the piperidine moiety; $R_2$ is alkylene or $-CO-(CH_2)_n-$ wherein n is 0 to 11, preferably from 3 to 9 carbon atoms; $R_3$ and $R_4$, independently, are hydrogen, halogen or lower alkoxy; and HET is pyridinyl, pyrimidinyl or imidazolyl and salts thereof with pharmaceutically acceptable acids.

As used herein, the term "lower alkoxy" denotes a straight or branched-chain radical of 1 to 7 carbon atoms, for example, methoxy, ethoxy, propoxy, isopropoxy, n-butoxy, tertitary-butoxy, peritoxy, hextoxy and the like. The term "alkylene" preferably denotes a straight or branched-chain radical of 1 to 12 carbon atoms, and more preferably from 4 to 10 carbon atoms, for example, methylene, ethylene, propylene, butylene, pentylene, hexylene, heptylene, octylene, nonylene, decylene, dodecylene and the like. The term "halogen" denotes chlorine, bromine, iodine and fluorine. The term "HET" denotes heterocyclic radicals, for example, pyridinyl, pyrimidinyl or imidazolyl; preferably, 3-pyridinyl, 5-pyrimidinyl or 1-imidazolyl.

A preferred group of compounds of formula I of the invention are those wherein $R_1$ is

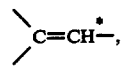

$R_2$ is alkylene of 1 to 12 carbon atoms; $R_3$ is hydrogen and HET is pyridinyl or pyrimidinyl.

A more preferred group of compounds of formula I of the invention are those wherein $R_1$ is

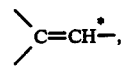

$R_2$ is alkylene of 4 to 10 carbon atoms, $R_3$ is hydrogen and HET is pyridinyl.

Preferred compounds of formula I of the invention are:
3-[8-[4-(2,2-diphenylethenyl)-1-piperidinyl]octyl]pyridine;
3-[7-[4-(2,2-diphenylethenyl)-1-piperidinyl]heptyl]pyridine (1:1)-(E)-2-butenedioate salt hemihydrate;
3-[6-[4-(2,2-diphenylethenyl)-1-piperidinyl]hexyl]pyridine (1:1)-(E)-2-butenedioate salt; and
3-[5-[4-(2,2-diphenylethenyl)-1-piperidinyl]pentyl]pyridine (1:1)-(E)-2-butenedioate salt.

The most preferred compound of formula I of the invention is 3-[8-[4-(2,2-diphenylethenyl)-1-piperidinyl]octyl]pyridine.

Examplary of the other compounds of formula I are:
3-[8-[4-[2,2-bis(3-fluorophenyl)ethenyl]-1-piperidinyl]octyl]pyridine;
3-[8-[4-[2,2-bis(2-fluorophenyl)ethenyl]-1-piperidinyl]octyl]pyridine;
1-[6-[4-[2,2-bis(4-fluorophenyl)ethenyl]-1-piperidinyl]hexyl]-1H-imidazole;
3-[8-[4-[2,2-bis(2-methoxyphenyl)ethenyl]-1-piperidinyl]octyl]pyridine;
1-[6-[4-[2,2-bis(4-methoxyphenyl)ethenyl]-1-piperidinyl]hexyl]-1H-imidazole;
5-[6-[4-[2,2-bis(3-fluorophenyl)ethenyl]-1-piperidinyl]hexyl]pyrimidine; and the like.

The compounds of formula I of the invention and intermediates for their preparation can be prepared as hereinafter described in Reaction Schemes I to IV.

REACTION SCHEME I

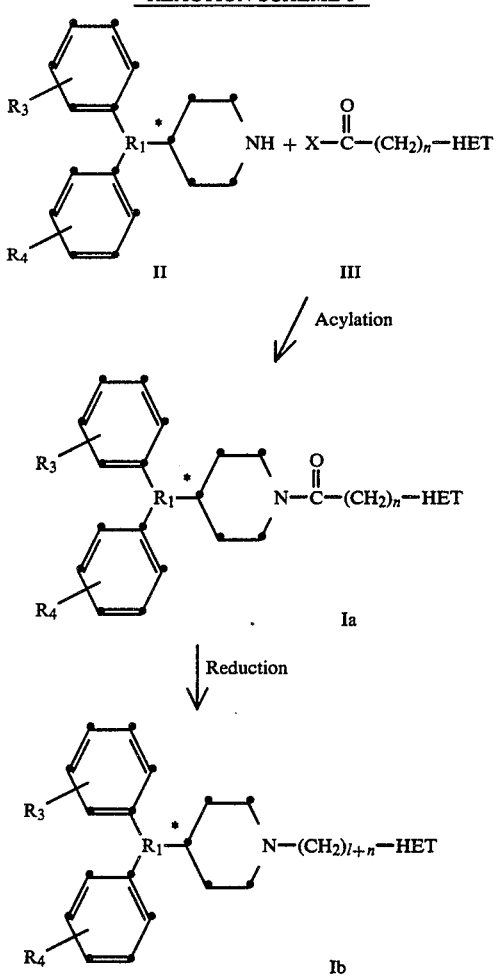

wherein $R_1$, $R_3$, $R_4$, n and HET are as previously described and X is halogen.

In Reaction Scheme I, it is initially noted that compounds of formula II, wherein $R_1$ is

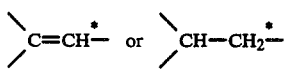

also form part of the invention, whereas those wherein $R_1$ is

are known or can be prepared according to known procedures. In the process, a compound of formula I is reacted, that is, acylated, with a compound of formula III, which are known or can be prepared according to known procedures, to form the corresponding compound of formula Ia. The acylation can be carried out according to known procedures. More particularly, it can be carried out in an aprotic solvent, for example, tetrahydrofuran, benzene, toluene or the like, preferably in dimethylformamide, and in the presence of a base, for example, pyridine, triethylamine or the like, at a temperature in the range of from about 0° C. to about the reflux temperature of the reaction mixture, preferably, at about 0° C. The obtained compound of formula Ia can be recovered utilizing conventional procedures, for example, crystallization, distillation, evaporation or the like.

The obtained compound of formula Ia can then, if desired, be reduced to a compound of formula Ib according to known procedures. More particularly, the reduction can be carried out in a solvent, for example, tetrahydrofuran, a hydrocarbon such as toluene or benzene, or the like, with hydride reducing agent, for example, lithium aluminum hydride, sodium bis(2-methoxyethoxy)aluminum hydride or the like, at a temperature in a range of from about 0° C. to about the reflux temperature of the reaction mixture, preferably at room temperature. The obtained compound of formula Ib can be recovered utilizing conventional procedures, for example, crystallization, distillation, evaporation or the like.

REACTION SCHEME II

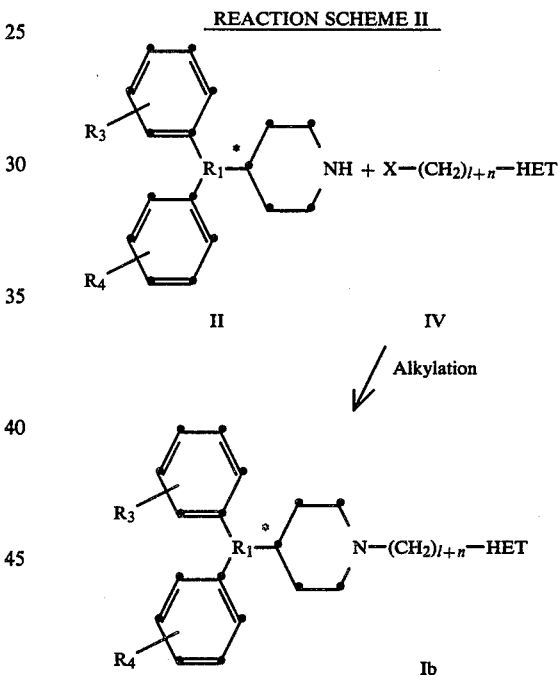

wherein $R_1$, $R_3$, $R_4$, X, HET and n are as previously described.

In Reaction Scheme II, a compound of formula II can also be reacted, that is, alkylated, with a compound of formula IV, which are known compounds or can be prepared according to known procedures, to form the corresponding compound of formula Ib. The alkylation can be carried out according to known procedures. More particularly, the alkylation can be carried out in a solvent, for example, dimethylformamide, dimethylsulfoxide, an alkanol such as ethanol, or the like, and in the presence of a base, for example, anhydrous sodium carbonate, sodium alkoxide such as sodium methoxide, aqueous alkali metal hydroxide such as sodium hydroxide or the like, at a temperature in the range of from about 0° C. to about 100° C., preferably a range of from about 50° C. to about 75° C. The obtained compound of formula I can be recovered utilizing conventional procedures, as hereinbefore described.

REACTION SCHEME III

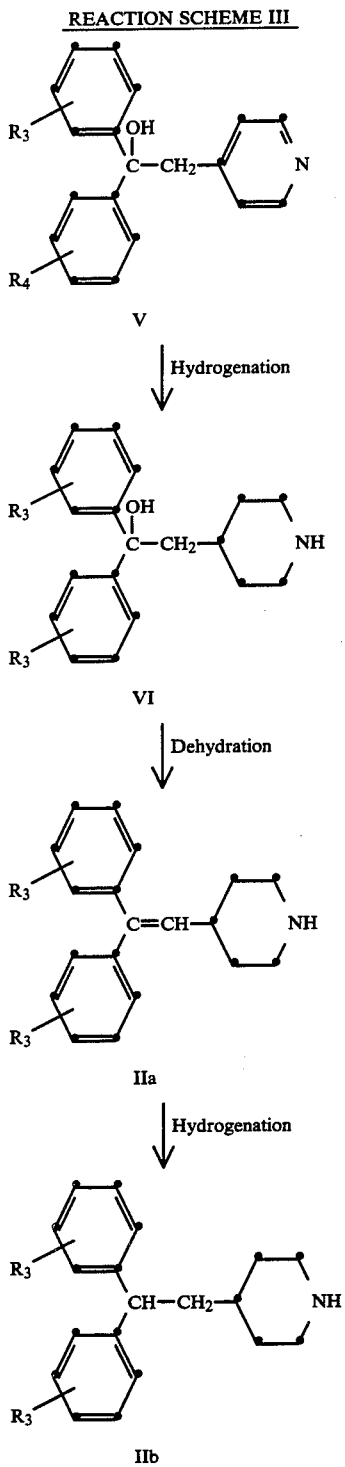

wherein $R_3$ and $R_4$ are as previously described.

In Reaction Scheme III, a compound of formula V, which are known compounds or can be prepared according to known procedures, is hydrogenated to give the corresponding compound of formula VI. The hydrogenation can be carried out according to known procedures. More particularly, the hydrogenation can be carried in a solvent, for example, glacial acetic acid, in the presence of a hydrogenation catalyst, for example, platinum oxide or the like, and hydrogen, at a pressure in the range of from atmospheric pressure to 100 psi, preferably about 50 psi, and at a temperature in the range of from about 0° C. to about 100° C., preferably in the range of from about 25° C. to about 50° C. The obtained compound of formula VI can be recovered utilizing known procedures, as hereinbefore described.

Thereafter, the obtained compound of formula VI is dehydrated utilizing known procedures to yield the corresponding compound of formula IIa. More particularly, the dehydration can be carried out in the presence of trifluoroacetic acid or the like, or, alternatively, with an acid such as toluenesulfonic acid in a hydrocarbon solvent such as toluene or benzene, at a temperature in the range of from about 0° to about 50° C., preferably at about 25° C. The obtained compound of formula IIa can be recovered utilizing known procedures, as hereinbefore described. It is desirable to isolate the obtained compound of formula IIa if it is to be hydrogenated to the corresponding compound of formula IIb.

If desired, a compound of formula IIa can be hydrogenated to yield the corresponding compound of formula IIb utilizing known procedures. More particularly, the hydrogenation can be carried in a solvent, for example, an alkanol such as ethanol, utilizing as the catalyst, for example, 10% palladium on carbon, in the presence of hydrogen at atmospheric pressure and at a temperature of 25° C. The obtained compound of formula IIb is recovered utilizing conventional procedures, as hereinbefore described.

REACTION SCHEME IV

HET—(CH$_2$)$_n$—OH

VII

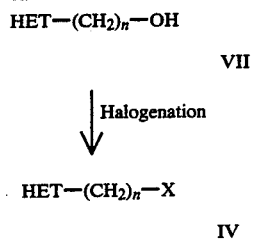

HET—(CH$_2$)$_n$—X

IV wherein, n, X and HET are as previously described.

In Reaction Scheme IV, a compound of formula VII, which are known compounds or can be prepared according to known procedures, can be halogenated utilizing known procedures. More particularly, the halogenation can be carried out with a halogenating agent, for example, thionyl chloride or the like, in a solvent, for example, a halogenated hydrocarbon such as methylene chloride, an aprotic solvent, or a hydrocarbon such as benzene or toluene, at a temperature in the range of from about 0° to about the reflux temperature of the reaction mixture, preferably at about the reflux temperature of the reaction mixture. The obtained compounds of formula IV can be recovered utilizing known procedures, as hereinbefore described.

The compounds of formula I form acid addition salts with pharmaceutically acceptable inorganic acids, for example, with hydrohalic acids such as hydrochloric acid, hydrobromic acid or hydroiodic acid, or with other mineral acids such as sulfuric acid, phosphoric acid, nitric acid, or the like, and with organic acids, for example, tartaric acid, citric acid, fumaric acid, camphor-sulfonic acid, methanesulfonic acid, toluenesulfonic acid, salicyclic acid, ascorbic acid, maleic acid, mandelic acid or the like. The preferred salts are the hydrohalides, especially the hydrochlorides, the maleates, the fumarates and the methanesulfonates. The pharmaceutically acceptable acid addition salts are preferably prepared in a suitable solvent, for example, ethanol, acetone or acetonitrile, by treating the free base with an appropriate nonaqueous acid.

The compounds of formula I of the invention as well as their pharmaceutically acceptable acid addition salts exhibit insulin lowering activity and are therefore useful as agents for the treatment of obesity. The insulin lowering activity can be demonstrated as hereinafter described.

DETERMINATION OF INSULIN-SECRETORY ACTIVITY IN THE ISOLATED PERFUSED RAT PANCREAS

Pancreases were obtained from young adult female Charles River rats weighing from 200-300 g. The animals were anesthesized with sodium pentobarbitol (45 mg/kg), injected intraperitoneally, and the pancreas with its intact vasculature was removed and connected to an extracorporeal perfusion apparatus.

The basic perfusion solution contained: 133 mM NaCl, 4.4 mM KCl, 2.5 mM $MgSO_4$, 2.4 mM Ca gluconate, 1.5 mM $KH_2PO_4$, 29.4 mM $HaHCO_3$, 4% dextran and 0.2% bovine serum albumin and glucose as discussed below. The perfusion flow rate was kept constant at 4 ml/min. After a 15-20 minute equilibration period, the experimental protocol was begun. The pancreatic effluent was collected in either one or four-minute fractions.

The perfusion was run in the following sequence for each test compounds:
10 min 5.6 mM glucose
30 min 16.7 mM glucose—internal control
10 min 5.6 mM glucose
30 min 16.7 mM glucose and test compound
10 min 16.7 mM glucose—to check pancreas viability The perfusion for the nontreated pancreas preparation was run as above, except that the test compound was omitted and replaced with perfusion solution.

Test compounds were dissolved in 90% ethanol or dimethylsulfoxide to a concentration of 25 mM and then diluted in the perfusion buffer to the desired concentration. The perfusion effluent was collected in one or four minute fractions—the samples were checked immediately, aliquoted for submission to radioimmunoassay and stored at $-20°$ C. until the time of assay. The radioimmunoassay of insulin was carried out by a back-titration method using a pure rat insulin standard.

To assess the inhibitory activity of the test compounds, an inhibition index was calculated. The inhibition index is derived by comparing the insulin secretion response from treated versus nontreated pancreas preparations. For each preparation, a ratio of insulin secretion was calculated from the area under the insulin secretion curve of the first pulse of 16.7 mM glucose divided by the area under the curve of the second pulse of 16.7 mM glucose containing compound.

The compounds of formula I of the invention significantly reduced insulin secretion in the perfused rat pancreas.

GLUCOSE CLEARANCE: ACUTE IN VIVO MODEL

The rationale for this test is that compounds which suppress insulin secretion should increase circulating glucose levels above those observed in controls following the administration of a high glucose load. Sprague-Dawley rats which range in weight from 150 to 180 grams after an overnight fast of 16 or 18 hours are given the test compound (100 mg/kg body weight) by intragastric administration 30 minutes before the intraperitoneal administration of glucose (1 g/kg body weight). Circulating glucose levels are determined immediately before glucose administration and 30, 60 and 90 minutes after glucose administration. Active compounds increase circulating glucose levels compared to controls. Since glucose levels peak at 30 minutes following glucose administration, the difference in circulating glucose levels between controls and treated rats at 30 minutes is used as an index of activity. The data are expressed as percent of control. Values significantly higher than 100% indicate activity.

The compounds of formula I of the invention which were utilized as test compounds in the foregoing tests and the results obtained are set out, hereinafter, in Table I.

TABLE I

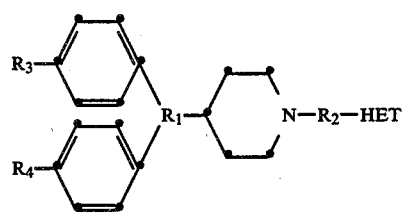

| $R_1$ | $R_2$ | $R_3$ | $R_4$ | HET | Perfused Pancreas conc. ($\mu$M) | Inhibition Index[a] | Glucose Clearance % of control |
|---|---|---|---|---|---|---|---|
| $>$CH— | —CO(CH$_2$)$_3$— | H | H | 3-pyridinyl | 100 | 6.0 | 105 |
| $>$C=CH— | —CO(CH$_2$)$_3$— | H | H | 3-pyridinyl | 50 | 7.6 | 99 |

TABLE I-continued

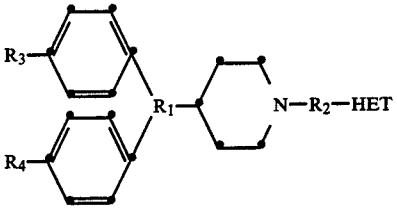

| R₁ | R₂ | R₃ | R₄ | HET | Perfused Pancreas conc. (μM) | Inhibition Index[a] | Glucose Clearance % of control |
|---|---|---|---|---|---|---|---|
| \C=CH—/ | —CO(CH₂)₃— | F | F | 3-pyridinyl | | | |
| \C=CH—/ | —CO(CH₂)₄— | H | H | 3-pyridinyl | | | |
| \CHCH₂—/ | —CO(CH₂)₃— | H | H | 3-pyridinyl | 100 | 14.1 | 109 |
| \CHCH₂—/ | —CO(CH₂)₃— | F | F | 3-pyridinyl | | | |
| \CH—/ | —(CH₂)₄— | H | H | 3-pyridinyl | 100 | 5.3 | 120 |
| \C=CH—/ | —(CH₂)₄— | H | H | 3-pyridinyl | 100 | 1.7 | 101 |
| \C=CH—/ | —(CH₂)₄— | F | F | 3-pyridinyl | 100 | 0.6 | 113 |
| \C=CH—/ | —(CH₂)₅— | H | H | 3-pyridinyl | 100 | 24.1 | 97 |
| \CHCH₂—/ | —(CH₂)₄— | H | H | 3-pyridinyl | 100 | 19.1 | 106 |
| \CHCH₂—/ | —(CH₂)₄— | F | F | 3-pyridinyl | 100 | 16.3 | 136 |
| \C=CH—/ | —(CH₂)₃— | H | H | 3-pyridinyl | 100 | 10.1 | 101 |
| \C=CH—/ | —(CH₂)₆— | H | H | 3-pyridinyl | 100 | 2.6 | 144 |

TABLE I-continued

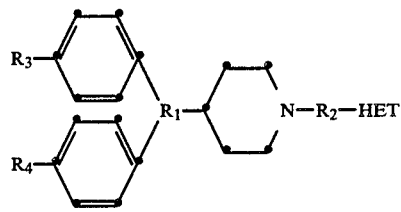

| $R_1$ | $R_2$ | $R_3$ | $R_4$ | HET | Perfused Pancreas conc. (μM) | Inhibition Index[a] | Glucose Clearance % of control |
|---|---|---|---|---|---|---|---|
| \C=CH—/ | —(CH$_2$)$_7$— | H | H | 3-pyridinyl | 50 | 35 | 118 |
| \C=CH—/ | —(CH$_2$)$_8$— | H | H | 3-pyridinyl | 50 | 38 | 127 |
| \CHCH$_2$—/ | —(CH$_2$)$_6$— | F | F | 3-pyridinyl | 50 | 2.0 | 125 |
| \CHCH$_2$—/ | —(CH$_2$)$_8$— | H | H | 3-pyridinyl | | | |
| \C=CH—/ | —(CH$_2$)$_4$— | H | H | 5-pyrimidinyl | 100 | 3.0 | 147 |
| \C=CH—/ | —(CH$_2$)$_6$— | H | H | 5-pyrimidinyl | 100 | 10.4 | 104 |
| \C=CH—/ | —CO(CH$_2$)$_8$— | H | H | 3-pyridinyl | 50 | 1.4 | 100 |
| \C=CH—/ | —(CH$_2$)$_9$— | H | H | 3-pyridinyl | 50 | 2.7 | 107 |
| \C=CH—/ | —(CH$_2$)$_{10}$— | H | H | 3-pyridinyl | 50 | — | 100 |
| \C=CH—/ | —CO(CH$_2$)$_5$— | H | H | 1-imidazolyl | 50 | 2.5 | 120 |
| \C=CH—/ | —(CH$_2$)$_6$— | H | H | 1-imidazolyl | 50 | 1.1 | 101 |

[a]The inhibition index is derived by comparing the insulin secretion response before and after perfusing an isolated rat pancreas with the test compound. An inhibition index greater than unity indicates a suppression of insulin secretion.

ANTIOBESITY EFFECTS IN OBESE ZUCKER RATS

Genetically Obese Male Zucker rats were kept in temperature (22° C.) and light (12 hours light-dark cycle) regulated rooms. One week prior to the start of the experiment, the rats were transferred to individual wire-bottomed cages and trained to eat a powdered chow diet (Ralston Purina Co., St. Louis, Mo.) ad libitum.

At the beginning of the experiment, the control group contributed to eat the chow diet and the experimental animals were given a chow diet containing drug. The amount of drug administered was calculated from the food intake per kg body weight for each experimental group. The age of the rats at the start of the drug treatment was two to three months. The period of treatment was 28 to 64 days. Food intake and body weights were recorded periodically (once each day to twice a week) throughout the duration of the study. Plasma samples for insulin and glucose determinations were taken from clipped tails. Carcass composition was determined at the end of the treatment period and, or comparative purposes, prior to the start of treatment.

3-[8-[4-(2,2-diphenylethenyl)-1-piperidinyl]octyl]-pyridine administration caused a dose dependent decrease in body weight, food intake and insulin levels in obese rats following 28 days of treatment. Glucose levels were unaltered by treatment. Reduced body weight in obese rats treated for 64 days could be accounted for by decreased carcass lipid.

The compounds of formula I of the invention which were utilized as test compounds in the foregoing tests and the results obtained are set out, hereinafter, in Tables II and III.

vegetable oils, gum arabic, polyalkyleneglycols or the like. The pharmaceutical preparations can be made up in solid form, for example, as tablets, dragees, suppositories or capsules, or in liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. They may also contain other therapeutically valuable substances.

Pharmaceutical dosage forms can contain about 250 mg. to 500 mg. of a compound of formula I or of its pharmaceutically acceptable acid addition salt. Oral dosages can comprise from abour 5 mg/kg per day to about 30 mg/kg per day. However, the foregoing ranges can be varied upwards or downwards according to the individual requirements of the host, that is, a warm-blooded animal.

The examples which follow further illustrate the invention. All temperatures are in degrees Centigrade, unless otherwise stated.

EXAMPLE 1

Preparation of 3-Pyridineoctanol

A mixture of 34.6 g of 7-octyn-1-ol 26.4 mL of 3-bromopyridine, 115 mL of triethylamine and 350 mL of dichloromethane was stirred and flushed with argon. To the mixture was added 3.85 g of bis triphenylphosphine palladium II chloride and 0.365 g of cuprous iodide and then the mixture was refluxed overnight. The cooled reaction mixture was diluted with ether and

TABLE II

Antiobesity activity of 3-[8-[4-(2,2-diphenylethenyl)-1-piperidinyl]-octyl]pyridine In Obese Zucker Rats

| Compounds of Formula I | Dose mg/kg | Body Weight Gain[c] g | Carcass Lipid Difference[d] g | Food Intake % of control | Circulating Insulin[a] % of control |
|---|---|---|---|---|---|
| 3-[8-[4-(2,2-diphenylethenyl)-1-piperidinyl]-octyl]pyridine[a] | 9 | +9 | nd | 91 | 83 |
| | 17 | −16 | nd | 89 | 76 |
| | 24 | −32* | nd | 82* | 47* |
| | 34 | −55* | nd | 83* | 33* |
| 3-[8-[4-(2,2-diphenylethenyl)-1-piperidinyl]-octyl]pyridine[b] | 28 | −88* | −62* | 81* | 47* |

[a]Treatment duration was 28 days.
[b]Treatment duration was 64 days.
[c]Body weight gain was computed by taking the difference between the weight gain of treated and control rats.
[d]Carcass lipid difference was computed by taking the difference between the carcass lipid content of treated and control rats.
[e]Circulating insulin levels were measured on the last day of treatment.
nd: Not determined.
*Significantly different from control; $p < 0.05$.

TABLE III

Antiobesity Activities of Representative Diphenylethenyls of Formula I

| Compounds of Formula I | Dose mg/kg | Body Weight Gain[a] g | Food Intake % of control | Relative Body Weight Gain Index[b] |
|---|---|---|---|---|
| 3-[8-[4-(2,2-diphenylethenyl)-1-piperdinyl]-octyl]pyridine | 38 | −49* | 73* | 92 |
| 3-[8-[4-(2,2-diphenylethyl)-1-piperdinyl]-octyl]pyridine | 58 | −76* | 70* | 94 |
| 4-(2,2-diphenylethenyl)-1-[1-oxo-9-(3-pyridinyl)nonyl piperidine | 49 | −12 | 100 | 17 |
| 3-[9-[4-(2,2-diphenylethenyl)-1-piperidinyl]-nonyl]pyridine | 41 | −35* | 82* | 61 |
| 3-[10-[4-(2,2-diphenylethenyl)-1-piperidinyl]decyl]pyridine | 46 | −46* | 91 | 71 |

[a]Body weight gain was computed by taking the difference between the weight gain of treated and control rats.
[b]Relative body weight gain index was computed by dividing the body weight gain by the number of treatment days (14) and then dividing by the dose (g/kg). It is used as a comparative measure of efficacy in which duration of treatment and dose have been normalized.

The compounds of formula I provided by the present invention can be used as medicaments, for example, in the form of pharmaceutical preparations which contain them in association with a compatible organic or inorganic inert carrier material suitable for enteral, for example, oral, or parenteral administration, for example, water, gelatin, lactose, starch, magnesium stearate, talc, the solids were filtered, washed well with ether, and then discarded. The filtrates were extracted repeatedly with 1N hydrochloric acid and the combined aqueous layers were made strongly basic with excess sodium hydroxide. The mixture was extracted with dichloromethane, dried over sodium sulfate and evaporated to provide 51 g (91%) of crude 8-(3-pyridinyl)-7-octyn-1-ol. Catalytic hydrogenation in 1000 mL of ethanol using 5 g of 10% palladium on carbon provided, after distillation, 36 g (72%) of 3-pyridineoctanol, bp 145°–152° C. (0.3 mm). Analysis Calculated for $C_{13}H_{21}NO$: C, 75.32; H, 10.21; N, 6.76. Found: C, 75.13; H, 10.21; N, 6.66.

EXAMPLE 2

Preparation of 5-Pyrimidinebutanol 5-bromopyrimidine and 3-butyn-1-ol was reacted as above, to give 5-pyrimidinebutanol as a colorless oil, bp 175°–180° C. (0.3 mm). Analysis Calculated for $C_8H_{12}N_2O$: C, 63.13; H, 7.95; N, 18.41. Found: C, 62.83; H, 7.98; N, 18.63.

EXAMPLE 3

Preparation of 5-Pyrimidinehexanol 5-bromopyrimidine and 5-hexyn-1-ol was reacted, as above, to give 5-pyrimidinehexanol as a colorless oil. bp 170°–175° C. (0.6 mm). Analysis Calculated for $C_{10}H_{16}N_2O$: C, 66.63; H, 8.95; N, 15.54. Found: C, 66.62; H, 9.15; N, 15.59.

General procedure for the preparation of heteroarylalkyl chlorides

A cold solution of 0.03 mole of the heteroarylalkyl alcohol in 40 mL of methylene chloride was treated dropwise with a solution of 0.04 mole of thionyl chloride in 10 mL of methylene chloride. The resulting solution was refluxed for 1 hour, chilled, and washed with saturated aqueous potassium carbonate solution. The organic layers were dried over sodium sulfate and evaporated at 25° C. The resulting oil was used without further purification.

General procedure for the preparation of heteroarylalkanoyl chlorides

Thionyl chloride (20 mL) was chilled in ice and the solid pyridine carboxylic acid was added. The mixture was stirred at 25° C. for 15 minutes and then evaporated to dryness several times from toluene. The resulting crude acid chloride hydrochloride was used without further purification.

EXAMPLE 4

Preparation of alpha, alpha-diphenyl-4-piperidine ethanol

The title compound was prepared by the hydrogenation of 40 g of alpha, alpha-diphenylpyridine ethanol at 50 psi in 500 mL of glacial acetic acid using 4.0 g of platinum oxide as catalyst. After filtration and evaporation, the solid residue was dissolved in a hot mixture of water and toluene, excess sodium hydroxide solution was then added and the resulting mixture was chilled and filtered. The crude product was recrystallized from toluene to provide 32.5 g (80%) of white solid, mp 153°–154° C. Analysis Calculated for $C_{19}H_{23}NO$: C, 81.10; H, 8.24; N, 4.98. Found: C, 80.73; H, 8.37; N, 4.82. The hydrochloride salt was crystallized from methanol, mp 271° C. (dec). Analysis Calculated for $C_{19}H_{23}NO.HCl$; C, 71.80; H, 7.61; H, 4.41; Cl, 11.15. Found: C, 71.75; H, 7.82; N, 4.30; Cl, 10.81.

EXAMPLE 5

Preparation of alpha,alpha-bis(4-fluorophenyl)-4-piperidineethanol. 0.25 molar methylbenzene solvate The title compound was prepared in the same manner as the compound of example 4 starting from alpha,alpha-bis(4-fluorophenyl)-4-pyridineethanol. Crystallization from toluene provided the toluene solvate, mp 161°–163° C. Analysis Calculated for $C_{19}H_{21}F_2NO.0.25 C_7H_8$: C, 73.21; H, 6.81; N, 4.11; F, 11.16. Found: C, 73.05; H, 7.08; N, 4.23; F, 10.81.

EXAMPLE 6

Preparation of 4-(2,2-diphenylethenyl)piperidine

The title compound was prepared by dissolving 20 g of alpha,alpha-diphenyl-4-piperidineethanol in 40 mL of anhydrous trifluoroacetic acid and stirring for 15 minutes. The volatiles were removed under vacuum and the residue was partitioned between toluene and 2N sodium hydroxide solution. The organic layers were dried over sodium sulfate, evaporated, and the residue was crystalized from hexane to give 17.2 g (92%) of 4-(2,2-diphenylethenyl)piperidine, mp 98°–99° C. Anal. Calcd for $C_{19}H_{21}N$: C, 86.65; H, 8,.04; N, 5.32. Found: C, 86.35; H, 7.97; N, 5.26.

EXAMPLE 7

Preparation of 4-[2,2-bis(4-fluorophenyl)ethenyl]piperidine, 0.15 molar hexanne solvate The title compound was prepared in the same manner as the compound of example 6, starting with 25 g of alpha,alpha-bis(4-fluorophenyl)-4-piperidineethanol, 0.25 molar methylbenzene solvate and 50 mL of trifluoroacetic acid. Crystallization from hexane gave 19.6 g (83%) of the hexane solvate of 4-[2,2-bis(4-fluorophenyl)ethenyl]-piperidine, mp 84°–86° C. Analysis Calculated for $C_{19}H_{19}F_2N.0.15C_6H_{14}$: C, 76.54; H, 6.81; N, 4.49; F, 12.17. Found: C, 76.87; H, 6.72; 4.65; F, 12.12.

EXAMPLE 8

Preparation of 4-(2,2-diphenylethyl)piperidine hydrochloride

The title compound was prepared by the hydrogenation of 15.2 g of 4-(2,2-diphenylethenyl)piperidine in 500 mL of ethyl alcohol using 1.5 g of 10% palladium on carbon as catalyst. After filtration and evaporation the resulting oil eventually solidified to a low melting wax. The hydrochloride salt was prepared and recrystallized from 2-propanol/ether to give the analytically pure salt 4-(2,2-diphenylethyl)piperidine hydrochloride, mp 178°–179° C. Analysis Calculated for $C_{19}H_{23}N.HCl$: C, 75.60; H, 8.01; H, 4.64; Cl, 11.74. Found: C, 75.50; H, 8.00; N. 4.57; Cl, 11.98.

EXAMPLE 9

Preparation of 4-[2,2-bis(4-fluorophenyl)ethyl]piperidine

The title compound was prepared in the same manner as 4-(2,2-diphenylethyl)piperidine HCl starting from 4-[2,2-bis(4-fluorophenyl)ethenyl]piperidine, 0.15 molar hexane solvate. The resulting clear, colorless, oil was used directly in the next steps.

EXAMPLE 10

Preparation of 4-diphenylmethyl-1-[1-oxo-4-(3-pyridinyl)butyl]piperidine, 0.1 molar ethylacetate solvate A mixture of 2.0 g of 4-diphenylmethylpiperidine in 5 mL of dimethylformamide and 4.2 mL of triethylamine was treated at 0° C. with a solution composed of 5 mL of dimethylformamide and the acid chloride prepared from 2.0 g of 3-pyridine butanoic acid. After 15 minutes the mixture was diluted with dichloromethane, filtered and evaporated to dryness. The residue was partitioned between toluene and 1N sodium hydroxide and the organic layer was washed with brine, dried over sodium sulfate and evaporated to give 3.3 g of crude oil. Purification was accomplished by chromatography on a Waters Prep 500 HPLC using silica gel columns and eluting with 98:2 ethyl acetate-triethylamine. The product consisted of a colorless oil which was dried under vacuum at 70° C. to give 2.8 g (86%) of 4-diphenylmethyl-1-[1-oxo-4-(3-pyridinyl)butyl]piperidine, 0.1 molar ethylacetate solvate. Analysis Calculated for $C_{27}H_{30}N_2O.O.1C_4H_8O_2$: C, 80.79; H, 7.62; N, 6.88. Found: C, 80.91; H, 7.57; N, 6.81.

EXAMPLE 11

Preparation of 4-(2,2-diphenylethenyl)-1-[1-oxo-4-(3-pyridinyl)butyl]-piperidine The title compound was prepared in a method similar to that employed for the compound of example 10 above starting with 7.9 g of 4-(2,2-diphenylethenyl)-piperidine and the acid chloride prepared from 6.6 g of 3-pyridine butanoic acid. Crystallization of the toluene extracts from dichloromethane/ether provided 9.1 g (74%) of 4-(2,2-diphenylethenyl-1-[1-oxo-4-(3-pyridinyl)butyl]piperidine, mp 91°–93° C. Analysis Calculated for $C_{28}H_{30}N_2O$: C, 81.91; H, 7.37; N, 6.82. Found: C, 81.88; H, 7.44; N, 6.81.

EXAMPLE 12

Preparation of 4-[2,2-bis(4-fluorophenyl)ethenyl]-1-[1-oxo-4-(3-pyridinyl)butyl]piperidine The title compound was prepared in a manner similar to that employed for the compound of example 10 starting with 9.0 g of 4-[2,2-bis(4-fluorophenyl)ethenyl]-piperidine, 0.15 molar hexane solvate and the acid chloride prepared from 6.6 g of 3-pyridine butanoic acid. The toluene extracts were evaporated and the residue was crystallized from ether to give 8.7 g (65%) of pure 4-[2,2-bis[4-fluorophenyl)ethenyl]1-[1-oxo-4-(3-pyridinyl)butyl]piperidine, mp 100°–102° C. Analysis Calculated for $C_{28}H_{28}F_2N_2O$: C, 75.31; H, 6.32; N, 6.27; F, 8.51. Found: C, 75.36; H, 6.30; N, 6.24; F, 8.30.

EXAMPLE 13

Preparation of 4-(2,2-diphenylethenyl)-1-[1-oxo-5-(3-pyridinyl)pentyl]-piperidine The title compound was prepared in a manner similar to that employed for the compound of example 10 starting with 5.27 g of 4-(2,2-diphenylethenyl)piperidine and the acid chloride prepared from 6.5 g of 3-pyridine pentanoic acid. The toluene extracts were evaporated and chromatographed on a Waters Prep 500 using silica gel columns and eluting with 98:2 ethyl acetate-triethylamine. Evaporation of the combined product fractions gave 8.0 g (94%) of crude 4-(2,2-diphenylethenyl)-1-[1-oxo-5-(3-pyridinyl)pentyl]piperidine. Crystallization of a small portion from ether gave analytically pure 4-(2,2-diphenylethenyl)-1-[1-oxo-5-(3-pyridinyl)pentyl]-piperidine, mp 82°–84° C. Analysis Calculated for $C_{29}H_{32}N_2O$: C, 82.04; H, 7.60; N, 6.60. Found: C, 81.88; H, 7.63; N, 6.67.

EXAMPLE 14

Preparation of 4-(2,2-diphenylethyl)-1-[1-oxo-4-(3-pyridinyl)butyl]-piperidine

The title compound was prepared in a manner similar to that employed for the compound of Example 10 starting with 5.3 g of 4-(2,2-diphenylethyl)piperidine free base and the acid chloride prepared from 5.0 g of 3-pyridine butanoic acid, there was obtained 7.0 g of oil from the toluene extracts. Crystallization from methylene chloride/ether provided 6.3 g (76%) of 4-(2,2-diphenylethyl)-1-[1-oxo-4-(3-pyridinyl)butyl]piperidine, mp 98°–100° C. Analysis Calculated for $C_{28}H_{32}N_2O$: C, 81.51; H, 7.82; N, 6.79. Found: C, 81.43; H, 7.88; N, 6.53.

EXAMPLE 15

Preparation of 4-[2,2-bis(4-fluorophenyl)ethyl]-1-[1-oxo-4-(3-pyridinyl)butyl]piperidine The title compound was prepared in a manner similar to that employed for the compound of Example 10 above starting with 8.3 g of 4-(2,2-diphenylethyl)piperidine and the acid chloride prepared from 6.1 g of 3-pyridine butanoic acid. The toluene extracts were evaporated and the residue was crystallized from methylene chloride/ether to give 10.5 g (85%) of pure 4-[2,2-bis(4-fluorophenyl)ethyl]-1-[1-oxo-4-(3-pyridinyl)butyl]-piperidine mp 108°–110° C. Analysis Calculated for $C_{28}H_{30}F_2N_2O$: C, 74.97; H, 6.74; N, 6.25; F, 8.47. Found: C, 75.15; H, 6.91; N, 6.21; F, 8.42.

EXAMPLE 16

Preparation of 3-[4-[4-(Diphenylmethyl)-1-piperidinyl]butyl]pyridine (1:1)-(Z)-2-butenedioate salt A solution of 7.8 g of the compound of Example 10 in 100 mL of toluene was stirred at ambient temperature and treated dropwise with 12 mL of a 3.5M solution of sodium bis(2-methoxyethoxy)aluminum hydride in toluene. After 30 minutes, the mixture was treated dropwise with excess 4N sodium hydroxide and extracted with toluene. The organic layers were washed with brine, dried over sodium sulfate and evaporated to give 6.9 g (90%) of pale yellow oil. A solution of 5.9 g of crude free base in 50 mL of hot ethanol was treated with 1.8 g of maleic acid and the solution was then diluted with 150 mL of ether. The resulting solid, mp 139°–140° C., was recrystallized as above to give 6.7 g (87%) of colorless 3-[4-[4-(diphenylmethyl)-1-piperidinyl]butyl]pyridine (1:1)-(Z)-2-butenedioate salt, mp 140°–141° C. Analysis Calculated for $C_{27}H_{32}N_2.C_4H_4O_4$: C, 74.37; H, 7.25; N, 5.60. Found: C, 74.38; H, 7.19; N, 5.59.

EXAMPLE 17

Preparation of
3-[4-[4-(2,2-Diphenylethenyl)-1-piperidinyl]butyl]pyridine

The title compound was prepared in a manner similar to that employed for 3-[4-[4-(diphenyl methyl)-1-piperidinyl]butyl]pyridine (1:1)-(Z)-2-butenedioate salt (Ex. 16) starting with 5.0 g of 4-(2,2-diphenylethenyl)-1-[1-oxo-4-(3-pyridinyl)butyl]piperidine and 7.2 mL of a 3.5M solution of sodium bis(2-methoxyethoxy)aluminum hydride in toluene. The analytically pure base was obtained from hexanne, mp 54°–56° C. Analysis Calculated for $C_{28}H_{32}N_2$: C, 84.80; H, 8.13; N, 7.06. Found: C. 84.61; H, 7.92; N, 7.05. Evaporation of the hexane filtrates provided 4.4 g of crude 3-[4-[4-(2,2-diphenylethenyl)-1-piperidinyl]butyl]pyridine, which was dissolved in 50 mL of hot ethanol and treated with 1.28 of fumaric acid. Dilution with 50 mL of ether provided 4.1 g (67%) of salt, mp 163°–165° C. Analysis Calculated for $C_{28}H_{32}N_2 \cdot C_4H_4O_4$: C, 74.97; H, 7.08; N, 5.46. Found: C, 74.69; H, 7.07; N, 5.44.

EXAMPLE 18

Preparation of
3-[4-[4-[2,2-bis(4-fluorophenyl)ethenyl]-1-piperidinyl]butyl]pyridine (1:1)-(E)-2-butenedioate salt The title compound was prepared in a manner similar to that employed for compound of Example 16 starting with 13.0 g of 4-[2,2-bis(4-fluorophenyl)ethenyl]-1-[1-oxo-4-(3-pyridinyl)butyl]piperidine and 34 mL of a 3.4M solution of sodium bis(2-methoxyethoxy)aluminum hydride in toluene. Evaporation of the toluene extracts and chromatography on 20 parts of silica gel in 1:1 hexane/ethyl acetate followed by elution of the product with 2% triethylamine in ethyl acetate gave 8.9 g of purified free base as an oil. This free base in 50 mL of hot methanol was treated with 2.3 g of fumaric acid and the methanol was removed by distillation while adding ethyl acetate. The resulting solids were recrystallized from methanol/ethyl acetate to give 8.9 g (56%) of pure 3-[4-[4-[2,2-bis(4-fluorophenyl)ethenyl]-1-piperidinyl]butyl]pyridine (1:1)-(E)-2-butenedioate salt, mp 183°–184° C. (dec). Analysis Calculated for $C_{28}H_{30}F_2N_2 \cdot C_4H_4O_4$: C, 70.06; H, 6.25; N, 5.11; F, 6.93. Found: C, 69.96; H, 6.41; N, 5.01; F, 7.15.

EXAMPLE 19

Preparation of
3-[5-[4-(2,2-Diphenylethenyl)-1-piperidinyl]pentyl]pyridine (1:1)-(E)-2-butenedioate salt The title compound was prepared in a manner similar to that employed for the compound of Example 16 starting with 7.4 g of 4-(2,2-diphenylethenyl)-1-[1-oxo-(5-(3-pyridinyl)pentyl]piperidine and 10.0 mL of a 3.5M solution of sodium bis(2-methoxyethoxy)aluminum hydride in toluene. Evaporation of the toluene extracts provided 7.4 g of free base as an oil. This free base in 50 mL of hot methanol was treated with 2.0 g of fumaric acid and the methanol was removed by distillation while adding ethyl acetate. The resulting solids were recrystallized as above to give 8.4 (92%) of pure 3-[4-[4-(2,2-Diphenylethenyl)-1-piperidinyl]pentyl]pyridine (1:1)-(E)-2-butenedioate salt, mp 160°–161° C. (dec). Analysis Calculated for $C_{29}H_{34}N_2 \cdot C_4H_4O_4$: C, 75.26; H, 7.27; N, 5.32. Found: C, 75.05; H, 7.28; N, 5.37.

EXAMPLE 20

Preparation of
3-[4-[4-(2,2-Diphenylethyl)-1-piperidinyl]butyl]pyridine

The title compound was prepared in a manner similar to that employed for the compound of Example 16 above. From 6.1 g of 4-(2,2-diphenylethyl)-1-[1-oxo-4-(3-pyridinyl)butyl]piperidine and 9 mL of a 3.5M solution of sodium bis(2-methoxyethoxy)aluminum hydride in toluene there was obtained 5.4 g (90%) of hexane crystallized free base 3-[4-[4-(2,2-diphenylethyl)-1-piperidinyl]butyl]pyridine, mp 62°–64° C. Analysis Calculated for $C_{28}H_{34}N_2$: C, 84.37; H, 8.60; N, 7.03. Found: C, 84.23; H, 8.59; N, 7.05. A solution of 5.25 g of free base and 1.53 g of fumaric acid in 30 mL of hot ethanol was diluted with 50 mL of ether and chilled. The resulting solid amounted to 6.4 g (96%) of fumarate salt, mp 146°–148° C. Analysis Calculated for $C_{28}H_{34}N_2 \cdot C_4H_4O_4$: C, 74.68; H, 7.44; N, 5.44. Found: C, 74.62; H, 7.38; N, 5.39.

EXAMPLE 21

Preparation of
3-[4-[4-[2,2-Bis(4-fluorophenyl)ethyl]-1-piperidinyl]butyl]pyridine (1:1)-(E)-2-butenedioate salt The title compound was prepared in a manner similar to that employed for the compound of Example 16. From 11.6 g of 4-[2,2-bis(4-fluorophenyl)ethyl]-1-[1-oxo-4-(3-pyridinyl)butyl]piperidine and 30 mL of 3.4M sodium bis(2-methoxyethoxy)aluminum hydride in toluene solution there was obtained 11.6 g of crude oil. Chromatography on 20 parts of silica gel in 1:1 hexane/ethylacetate followed by elution of the product with 2% triethylamine in ethylacetate gave 7.4 g (65%) of purified free base as an oil. A solution of 7.4 g of free base and 2.0 g of fumaric acid in 50 mL of methanol was diluted with ethyl acetate and chilled. Filtration and recrystallization from tetrahydrofuran/ether provided 7.1 g (76%) of pure 3-[4-[4-[2,2-bis(4-fluorophenyl)ethyl]-1-piperidinyl]butyl]pyridine (1:1)-(E)-2-butenedioate salt, mp 155°–156° C. (dec). Analysis Calculated for $C_{28}H_{32}F_2N_2 \cdot C_4H_4O_4$: C, 69.80; H, 6.59; N, 5.09; F, 6.90. Found: C, 69.75; H, 6.62; N, 5.05; F, 6.79.

EXAMPLE 22

Preparation of
3-[3-[4-(2,2-Diphenylethenyl)-1-piperidinyl]propyl]pyridine (1:1)-(E)-2-butenedioate salt The title compound was prepared by stirring a mixture of 4.0 g of 4-(2,2-diphenylethenyl)piperidine, 4.64 g of 3-(3-bromopropyl)-pyridine hydrobromide, 8.25 mL of 4N sodium hydroxide, and 50 mL of dimethylformamide at 25° C. for 3 hours. The volatiles were removed and the residue was partitioned between ethyl acetate and 1N sodium hydroxide. The organic layers were dried over sodium sulfate, evaporated, and the residue (5.8 g) was chromatographed on a Waters Prep 500 eluting with 96:2:2 ethyl acetate-methanol-triethylamine. The product fractions were combined and evaporated to give 4.9 g (85%) of free base as an oil. A solution of 4.9 g of free base in methanol was treated with 1.5 g of fumaric acid and the methanol was removed by distillation while adding ethyl acetate. The resulting solids were recrystallized from methanol/ethyl acetate to give 4.3 g (66%) of 3-[3-[4-(2,2-diphenylethenyl)-1- piperidinyl]propyl]pyridine (1:1)-(E)-2-butenedioate salt, mp 154°–156° C. (dec). Analysis Calculated for $C_{27}H_{30}N_2 \cdot C_4H_4O_4$: C, 74.67; H, 6.87; N, 5.62. Found: C, 74.71; H, 6.94; N, 5.68.

EXAMPLE 23

Preparation of 3-[6-[4-(2,2-diphenylethenyl)-1-piperidinyl]hexyl]pyridine (1:1)-(E)-2-butenedioate salt The title compound was prepared by heating a mixture of 4.64 g of 4-(2,2-diphenylethenyl)piperidine, 3.7 g of 3-(6-chlorohexyl)pyridine, 2.64 g of sodium iodide, and 50 mL of dimethylformamide at 50° C. for 18 hours. The solvent was evaporated and the residue was partitioned between 1N sodium hydroxide and ethyl acetate. The resulting oil (7.4 g) was chromatographed on a Waters Prep 500 using silica gel columns and eluting with 98:2 ethyl acetate-triethylamine. Evaporation of the product fractions provided 3.9 g (52%) of free base as an oil. A solution of 3.9 g of free base in 25 mL of hot methanol was treated with 1.07 g of fumaric acid and the methanol was removed by distillation while adding ethyl acetate. The resulting solids were recrystallized as above to give 4.0 g (82%) of 3-[6-[4-(2,2-diphenylethenyl)-1-piperidinyl]hexyl]pyridine (1:1)-(E)-2-butenedioate salt, mp 170°–172° C. (dec). Analysis Calculated for $C_{30}H_{36}N_2 \cdot C_4H_4O_4$: C, 75.53; H, 7.46; N, 5.18. Found: C, 75.39; H. 7.39; N, 5.42.

EXAMPLE 24

Preparation of 3-[7-[4-(2,2-Diphenylethenyl)-1-piperidinyl]heptyl]pyridine (1:1)-(E)-2-butenedioate salt hemihydrate The title compound was prepared in a manner similar to that employed for the compound of Example 23 above starting with 3.9 g of 4-(2,2-diphenylethenyl)piperidine, 3.1 g of 3-(7-chloroheptyl)pyridine, 2.2 g of sodium iodide, and 50 mL of dimethylformamide. Chromatography of the crude extracts as above provided 4.0 g (62%) of free base as an oil. Crystallization of the fumaric acid salt from methanol/ethyl acetate provided pure 3-[7-[4-(2,2-diphenylethenyl)-1-piperidinyl]heptyl]pyridine (1:1)-(E)-2-butenedioate salt hemihydrate, mp 96°–99° C. (dec). Analysis Calculated for $C_{31}H_{38}N_2 \cdot C_4H_4O_4 \cdot 0.5H_2O$: C, 74.57; H, 7.69; N, 4.97; $H_2O$, 1.60. Found: C, 74.79; H, 7.64; N, 4.97, $H_2O$, 1.50.

EXAMPLE 25

Preparation of 3-[8-[4-(2,2-diphenylethenyl)-1-piperidinyl]octyl]pyridine

The title compound was prepared in a manner similar to that employed for the compound of Example 23 above starting with 8.64 g of 4-(2,2-diphenylethenyl)-piperidine, 7.4 g of 3-(8-chlorooctyl)pyridine, 4.92 g of sodium iodide, 3.48 g of sodium carbonate, and 50 mL of dimethylformamide. The mixture was stirred an heated at 75° C. for 18 hours and then evaporated to dryness. The residue was partitioned between ethyl acetate and 1N sodium hydroxide and the organic layers were dried over sodium sulfate and evaporated to give 11.0 g (74%) of crude free base. Recrystallization from hexane gave the analytically pure, 3-[8-[4-(2,2-diphenylethenyl)-1-piperidinyl]octyl]pyridine, mp 54°–55° C. Analysis Calculated for $C_{32}H_{40}N_2$: C, 84.91; H, 8.91; N, 6.19. Found: C, 84.81; H, 8.74; N, 6.14. The fumaric acid salt was crystallized from ethanol/acetone, mp 128°–129° C. Analysis Calculated for $C_{32}H_{40}N_2 \cdot C_4H_4O_4$: C, 76.02; H, 7.80; N, 4.93. Found: C, 76.15, H, 7.79, N, 4.89.

EXAMPLE 26

Preparation of 3-[6-[4-[2,2-Bis(4-fluorophenyl)ethyl]-1-piperidinyl]-hexyl]pyridine (1:1)-(E)-2-butenedioate salt A mixture of 7.4 g of 3-(6-chlorohexyl)pyridine, 10.3 g of 4-[2,2-bis(4-fluorophenyl)ethyl]piperidine, 5.6 g of sodium iodide and 100 mL of dimethylformamide was stirred and heated at 50° C. for 18 hours and at 100° C. for 1 hour. The solvent was evaporated and the residue was partitioned between ethyl acetate and 1N sodium hydroxide. The dried over sodium sulfate organic layers were evaporated and the crude product (17.5 g) was chromatographed on a Waters Prep 500 HPLC eluting with 50:50:2 hexane-ethyl acetate-triethylamine. The product fractions were combined and evaporated to give 8.5 g (53%) of free base as an oil. A solution of 8.5 g of free base in methanol was treated with 2.13 g of fumaric acid and the methanol was removed by distillation while adding ethyl acetate. The resulting solids were recrystallized from methanol/ethyl acetate to give 7.5 g (72%) of 3-[6-[4-[2,2-bis(4-fluorophenyl)ethyl]-1-piperidinyl]hexyl]pyridine (1:1)-(E)-2-butenedioate salt, mp 140°–141° C. Analysis Calculated for $C_{30}H_{36}F_2N_2 \cdot C_4H_4O_4$: C, 70.57; H, 6.97; N, 4.84; F, 6.57. Found: C, 70.42; H, 7.08; N, 4.75; F, 6.27.

EXAMPLE 27

Preparation of 3-[8-[4-(2,2-Diphenylethyl)-1-piperidinyl]octyl]pyridine

The title compound was prepared by the hydrogenation of 7.3 g of 3-[8-[4-(2,2-diphenylethenyl)-1-piperidinyl]octyl]pyridine at ambient conditions using 100 mL of ethanol and 1.5 g of 10% palladium on carbon catalyst. After filtration and evaporation, the residue was crystallized from hexane to give 6.0 g (82%) of 3-[8-[4-(2,2-diphenylethyl)-1-piperidinyl]octyl]pyridine, mp 68°–70° C. Analysis Calculated for $C_{32}H_{42}N_2$: C, 84.53: H, 9.31; N, 6.16. Found: C, 84.68; H, 9.15; N, 6.12. The fumarate salt was crystallized from acetone, mp 110°–111° C. Analysis Calculated for $C_{32}H_{42}N_2 \cdot C_4H_4O_4$: C, 75.76; H, 8.12; N, 4.91. Found: C, 75.59; H, 8.00; N, 4.83.

EXAMPLE 28

Preparation of 5-[4-[4-(2,2-diphenylethenyl)-1-piperidinyl]butyl]-pyrimidine (1:1)-(E)-2-butenedioate salt The title compound was prepared in a manner similar to that employed for 3-[6-[4-(2,2-diphenylethenyl)-1-piperidinyl]hexyl]pyridine (1:1)-(E)-2-butenedioate starting with 4.64 g of 4-(2,2-diphenylethenyl)piperidine and 3.0 g of 5-(4-chlorobutyl)pyrimidine from 5-pyrimidinebutanol. Chromatography provided 3.6 g (52%) of free base as an oil. Crystallization of the fumaric acid salt from methanol/ethyl acetate gave 3.0 g of 5-[4-[4-(2,2-diphenylethenyl)-1-piperidinyl]butyl]-pyrimidine (1:1)-(E)-2-butenedioate salt, mp 181°–182° C. Analysis Calculated for $C_{27}H_{31}N_3 \cdot C_4H_4O_4$: C, 72.49; H, 6.87; N, 8.18. Found: C, 72.29; H, 6.90; N, 8.04.

EXAMPLE 29

Preparation of
5-[6-[4-(2,2-Diphenylethenyl)-1-piperidinyl]hexyl]-pyrimidine

The title compound was prepared in a manner similar to that employed for the compound of Example 23 starting with 7.4 g of 4-(2,2-diphenylethenyl)piperidine and 5.9 g of 5-(6-chlorohexyl)pyrimidine, from 5-pyrimidinehexanol. Chromatography provided 5.9 g (50%) of crude 5-[6-[4-(2,2-diphenylethenyl)-1-piperidinyl]hexyl]pyrimidine. Crystallization from hexane provided the analytically pure 5-[6-[4-(2,2-diphenylethenyl)-1-piperidinyl]hexyl]pyrimidine, mp 88°-90° C. Analysis Calculated for $C_{29}H_{35}N_3$: C, 81.84; H, 8.29; N, 9.87. Found: C, 81.90; H, 8.31; N, 9.78.

EXAMPLE 30

Preparation of
4-(2,2-Diphenylethenyl)-1-[1-oxo-9-(3-pyridinyl)-nonyl]piperidine The title compound was prepared in a manner similar to that employed for the compound of Example 10 starting with 7.9 g of 4-(2,2-diphenylethenyl)piperidine and the acid chloride prepared from 8.24 g of 3-pyridinenonanoic acid. The toluene extracts were evaporated and the residue was crystallized from ether to give 12.4 g (73.7%) of 4-(2,2-diphenylethenyl)-1-[1-oxo-9-(3-pyridinyl)nonyl]piperidine, mp 82°-83° C. Analysis Calculated for $C_{33}H_{40}N_2O$: C, 82.46; H, 8.39; N, 5.83. Found: C. 82.76; H. 8.33; N, 5.83.

EXAMPLE 31

Preparation of
3-[9-[4-(2,2-Diphenylethenyl)-1-piperidinyl]nonyl]pyridine

The title compound was prepared in a manner similar to that employed for the compound of Example 16 starting with 6.5 g of 4-(2,2-diphenylethenyl)-1-[1-oxo-9-(3-pyridinyl)nonyl]piperidine and 7.7 mL of a 3.5M solution of sodium bis(2-methoxyethoxy)aluminum hydride in toluene. The analytically pure base was obtained from hexane, mp 51°-53° C. Analysis Calculated for $C_{33}H_{42}N_2$: C. 84.93; H, 9.07; N, 6.00. Found: C, 85.20; H, 9.00; N, 6.05. Evaporation of the hexane filtrates provided 5.9 g of crude product, which was dissolved in 25 mL of hot methanol and treated with 1.47 g of fumaric acid. The methanol was removed by distillation while adding acetone and the resulting solids were recovered and recrystallized from methanol/acetone to give 6.7 g (85%) of pure fumarate salt of 3-[9-[4-(2,2-diphenylethenyl)-1-piperidinyl]nonyl]pyridine, mp 125°-127° C. Analysis Calculated for $C_{33}H_{42}N_2.C_4H_4O_4$: C, 76.26; H, 7.96; N, 4.81. Found: C, 76.54; H, 7.92; N, 4.90.

EXAMPLE 32

Preparation of
3-[10-[4-(2,2-Diphenylethenyl)-1-piperidinyl]decyl]-piperidine

The title compound was prepared in a manner similar to that employed for the compound of Example 23 starting with 6.59 g of 4-(2,2-diphenylethenyl)piperidine, 6.4 g of 3-(10-chlorodecyl)pyridine, 3.75 g of sodium iodide, 2.65 g of anhydrous sodium carbonate, and 40 mL of dimethylformamide. The mixture was heated at 75° for 18 hours and the solvent was evaporated. The residue was partitioned between 1N sodium hydroxide and ethyl acetate and the organic layer was removed, dried over sodium sulfate, decolorized with charcoal, filtered, and evaporated to give 10.4 g (86%) of product as a colorless oil. Crystallization from hexane provided the pure 3-[10-[4-(2,2-Diphenylethenyl)-1-piperidinyl]-decyl]pyridine, mp 63°-65° C. Analysis Calculated for $C_{34}H_{44}N_2$: C, 84.95; H, 9.23; N, 5.83. Found: C. 85.21; H 9.27; N, 5.84. The fumaric acid salt was obtained from acetone, mp 134°-136° C. Analysis Calculated for $C_{34}H_{44}N_2.C_4H_4O_4$: C, 76.48; H, 8.11; N, 4.69. Found: C, 76.53; H, 8.17; N, 4.88.

EXAMPLE 33

Preparation of
4-(2,2-Diphenylethenyl)-1-[1-oxo-6-(1H-imidazo-1-yl)hexyl]piperidine The title compound was prepared in a manner similar to that employed for the compound of Example 10 starting with 3.4 g of 4-(2,2-diphenylethenyl)piperidine and the acid chloride prepared from 2.73 g of 6-(1H-imidazol-1-yl)hexanoic acid. The toluene extracts were evaporated and chromatographed on a Waters Prep 500 using silica gel columns and eluting with 95:5:2 ethyl acetate-methanol-triethylamine. Evaporation of the combined product fractions and crystallization from ethyl acetate/hexane provided 4.7 g (84%) of 4-(2,2-Diphenylethenyl)-1-[1-oxo-6-(1H-imidazo-1-yl)hexyl]-piperidine, mp 98°-100° C. Analysis Calculated for $C_{28}H_{33}N_3O$: C, 78.65; H, 7.78; N, 9.83. Found: C, 78.90; H, 7.83; N, 9.92.

EXAMPLE 34

Preparation of
1-[6-[4-(2,2-Diphenylethenyl)-1-piperidinyl]hexyl]-1H-imidazole

The title compound was prepared in a manner similar to that employed for the compound of Example 16 starting with 2.5 g of 4-(2,2-diphenylethenyl)-1-[1-oxo-6-(1H-imidazo-1-yl)hexyl]piperidine and 3.4 mL of a 3.5M solution of sodium bis(2-methoxyethoxy)aluminum hydride in toluene. The resulting crude product was chromatographed on a Waters Prep 500 using silica gel columns and eluting with 95:5:2 ethyl acetate-methanol-triethylamine. Evaporation of the combined product fraction and crystallization from ether/hexane provided 1.7 g (70%) of 1-[6-[4-(2,2-Diphenylethenyl)-1-piperidinyl]hexyl]-1H-imidazole, mp 104°-106° C. Analysis Calculated for $C_{28}H_{35}N_3$: C, 81.31; H, 8.53; N, 10.16. Found: C, 81.43; H, 8.35; N, 10.12.

EXAMPLE 35

Preparation of alpha,alpha-diphenyl-4-pyridineethanol

A flame-dried, 12-L flask equipped with a mechanical stirrer, thermometer, and dropping funnel was charged under argon with 252.5 g of 4-picoline and 2.50 L of tetrahydrofuran. The solution was cooled in an ice bath to below 20° and maintained at 15°-20° during the addition over 15 minutes, of 1.315 L of 1.85M phenyllithium in 70:30 cyclohexane:ether solution. The mixture was stirred at 15°-20° for 30 minutes and then cooled to −5°-0° in an acetone-ice bath. The temperature was maintained in this range during the rapid addition of a solution of 494.2 g of benzophenone in 1.50 L tetrahydrofuran. A bright blue color persisted after the addition of just a little of the benzophenone solution. The cooling bath was removed and the mixture was stirred at ambient temperature for 3 hours. To the flask was added 1.0 L of deionized water and 2.0 L of tetrahydrofuran. The mixture was warm gently on a steam bath to dissolve all the solids. The aqueous phase was separated and extracted with 2.0 L of tetrahydrofuran. The combined organic solutions were dried over sodium sulfate and stripped of solvent on a rotary evaporator at 45°. The resulting solid was triturated at reflux with 1.60 L of hexanes. The suspension was stored at 4° overnight and filtered. The solids were washed with a total of 1.0 L of boiling point 35°–60° petroleum ether and dried in a forced air oven at 75° to give 699.6 g (94% yield) of alpha,alpha-diphenyl-4-pyridineethanol as a pale-yellow solid, mp 154°–155°.

EXAMPLE 36

Preparation of alpha,alpha-diphenyl-4-piperidineethanol

A glass autoclave liner was charged with 260 g of alpha,alpha-diphenyl-4-pyridineethanol, 3.0 L of 2B ethanol, and 26 g of 5% rhodium on carbon as catalyst. The mixture was hydrogenated at 85° and 130 psi until uptake ceased. about 6–12 hours. The cooled mixture was filtered to remove the catalyst and stripped on a rotary evaporator at 45° to give 258 g of tannish solid. Gas chromatography indicated 3% remaining alpha,alpha-diphenyl-4-pyridineethanol and 78% alpha,alpha-diphenyl-4-piperidine-ethanol. This material was taken up in 3.0 L of acetonitrile at reflux. The solution was stored at 4° overnight and filtered. The solid was washed with cold acetonitrile, air-dried, and recrystallized in the same manner from 2.50 L of acetonitrile. There was thus obtained 151.9 g of white solid having a gas chromatography purity of >96%. The mother liquors from the first recrystallization were concentrated on a rotary evaporator to about 1/5 of the original volume. The resulting solution was stored at −20° overnight and filtered. The solid was washed with cold acetonitrile and air dried to give 69.4 g of white solid having a gas chromatography purity of 85%. Two crystallizations of this material from acetonitrile gave 41.75 g of alpha,alpha-diphenyl-4-piperidineethanol havings a gas chromatography purity of >96% as a white solid. The combined materials (190.65 g=72% yield) were used in Example 37.

EXAMPLE 37

Preparation of 4-(2,2-diphenylethenyl)piperidine

A 2-L flask equipped with a thermometer, magnetic stirrer, and argon inlet was charged with 277 g alpha,alpha-diphenyl-4-piperidineethanol and 560 mL of trifluoroacetic acid. The exothermic reaction mixture warmed to 80° within a few minutes. The resulting dark brown solution was stirred at ambient temperature for 1.0 hour and stripped on a rotary evaporator at 40° to a yellow paste. This material was partitioned between 2.0 L of ether and 200 mL of 10% sodium hydroxide solution. The aqueous phase was extracted with 1.0 L of ether. The combined organic solutions were dried over sodium sulfate and stripped on a rotary evaporator at 45° to give 265 g of off-white solid. This material was taken up, at reflux, in 2.0 L of hexanes and 200 mL of tetrahydrofuran. The solution was concentrated to a volume of 1.0 L by distillation at atmospheric pressure and then stored at 4° overnight. The solid was collected by filtration, washed with a total of 1.0 L of boiling point 35°–60° petroleum ether, and air-dried to give 232.9 g of off-white solid. Concentration of the mother liquors and washings led to an additional 18.3 g of 4-(2,2-diphenylethenyl)piperidine. The combined products (251.2 g=97% yield) had mp 96°–97°.

EXAMPLE 38

Preparation of 7-Octyn-1-ol

A flame-dried, 12-L flask equipped with a mechanical stirrer, condenser, thermometer, and argon bubbler was charged with 6.40 L of 1,3-diaminopropane and 15 g of lithium wire. The mixture was warmed to 65° in an oil bath as the lithium dissolved exothermically. An additional 153 g of lithium wire was added portionwise over 2 hours as the temperature rose to 103°. The deep blue color was discharged 20 minutes after the end of the addition. The solution was brought to 20° with an ice bath and 1.56 kg of potassium tert.-butoxide was added in one portion. The yellow-brown solution was stirred at 20° for 15 minutes and 500 g of 3-octyn-1-ol (about 90% pure by gas chromatography), rinsed in with 100 mL of tetrahydrofuran, was added. The mixture was stirred at 20° overnight (for convenience only; gas chromatography showed the reaction to be complete after 15–30 minutes). The mixture was poured with vigorous stirring into 12 L of ice-water. An additional 8 L of ice was added to bring the temperature to 20° and the total was extracted with 3×8 L=24 L of methylene chloride. The combined extracts were washed with 8.0 L of deionized water, 8.0 L of 1N hydrochloric acid, and 4.0 L of brine and dried over sodium sulfate. Solvent removal on a rotary evaporator at 45° gave 510 g of a brown oil. Two distillations of this material through a 30-cm, vacuum-jacketed Vigreux column gave 338.2 g (68% yield) of 7-octyn-1-ol as a colorless liquid, bp 104°/12 mm. The material was homogeneous to gas chromatography.

EXAMPLE 39

Preparation of 8-(3-Pyridinyl)-7-octyn-1-ol

A flame-dried, 22-L flask equipped with a mechanical stirrer, condenser, and a gas inlet tube dipping below the surface of the solvent was charged with 4.0 L of methylene chloride, 1.25 L of triethylamine, 385 g of 7-octyn-1-ol, and 285 mL (456 g) of 3-bromopyridine. The reagents were rinsed into the flask with an additional 100 mL of methylene chloride. Argon was bubbled through the reaction mixture for 30 minutes. The flask was evacuated for 3 minutes at 70 mm. The vacuum was released by bubbling in argon. This process was repeated six times and then 42 g of dichlorobis(-triphenyl phosphine)palladium (II) and 4 g of cuprous iodide were added. The mixture was heated at a gentle reflux for 18 hours and cooled to 20°. To the mixture was added, with vigorous stirring, 8.0 L of ether. A small amount of yellowish-white solid was removed by filtration and washed with 2×1.5 L=3.0 L of ether. The combined filtrate was washed with 3.0 L of deionized water and 2×3.0 L=6.0 L of 1N hydrochloric acid. The combined aqueous solutions were washed with 2×2.5 L=5.0 L of ether. The organic solutions were discarded and the aqueous solution was made strongly basic by the addition of 2.50 L of 20% sodium hydroxide solution. The resulting mixture was extracted with 3×4.0 L=12.0 L of methylene chloride. The extracts were dried over sodium sulfate and filtered through Celite. Solvent removal on a rotary evaporator at 45° gave 534.2 g (91% yield) of a pale brown 8-(3-pyridinyl)-7-octyn-1-ol having a strong odor of 3-bromopyridine. No further purification of this material was undertaken.

EXAMPLE 40

Preparation of 3-Pyridineoctanol

A glass autoclave liner was charged with 534.2 g of 8-(3-pyridinyl)-7-octyn-1-ol, 3.0 L, of 2B ethanol, and 50 g of 5% palladium on carbon catalyst. The mixture was hydrogenated at 100 psi and ambient temperature (exotherm to 45°) for 20 hours. The catalyst was removed by filtration and rinsed with fresh solvent. The filtrate was concentrated on a rotary evaporator at 45° to a yellow semi-solid paste. This material was partitioned between 4.0 L of ether and 2.5 L of 3N sodium hydroxide. The aqueous phase was extracted with 2×2.0 L=4.0 L of ether. The combined ether solutions were washed with 3.0 L of brine and dried over sodium sulfate. Solvent removal on a rotary evaporator at 45° gave 396.2 g of dark oil. Distillation of this material through a 30-cm, vacuum-jacketed Vigreux column gave 324.2 g (54% yield from 3-bromopyridine) of 3-pyridineoctanol as a colorless oil, bp 103°-104°/0.35-0.4 mm. Gas chromatography analysis showed this material to be homogeneous.

EXAMPLE 41

Preparation of 3-(8-Chlorooctyl)pyridine

A 3-L flask equipped with a mechanical stirrer, thermometer, and addition funnel was charged with 145.8 g of 3-pyridineoctanol and 1.0 L of methylene chloride. The solution was cooled in an ice bath and 72 mL of thionyl chloride, diluted to 500 mL with methylene chloride, was added dropwise over 15 minutes. The cooling bath was removed and the mixture was heated at a gentle reflux for 1.0 hour. The mixture was again cooled in an ice bath and treated with 750 mL of 3N sodium hydroxide. The separated aqueous phase was extracted with 2×250 mL=500 mL of methylene chloride. The combined organic solutions were dried over sodium sulfate to which was added 10 g of Norite A charcoal. The mixture was filtered through Celite and the solvent was stripped on a rotary evaporator at 45°. The residue was co-stripped with 100 mL of toluene to give 191.3 g (overweight) of the desired 3-(8-chlorooctyl)pyridine as a brown oil which was used without further purification.

EXAMPLE 42

Preparation of 3-[8-[4-(2,2-diphenylethenyl)-1-piperidinyl]octyl]pyridine

A 5-L flask equipped with a magnetic stirrer, condenser, and argon inlet tube was charged with the 191.3 g of crude, overweight 3-(8-chlorooctyl)-pyridine, 184.4 g of 4-(2,2-diphenylethenyl)piperidine, 1.0 L of N,N-dimethylformamide, 116.3 g of potassium iodide, and 74.2 g of potassium carbonate. The mixture was stirred and heated at 75° for 18 hours and then cooled to 20°. Most of the solvent was removed on a rotary evaporator at 50°/0.5 mm. The residual yellow-brown semi-solid was partitioned between 2.0 L of ether and 1.0 L of deionized water. The aqueous layer was extracted with 2×1.0 L=2.0 L of ether. The combined ether solutions were washed with 500 mL of deionized water and 500 mL of brine and dried over sodium sulfate, to which was added 20 g of Norit SG Extra charcoal. This mixture was filtered through Celite and concentrated on a rotary evaporator at 45° to an oil which solidified upon standing. The solid was triturated with 500 mL of warm hexanes. The suspension was stored overnight at −20° and filtered. The solid was washed with a total of 100 mL of cold hexanes and dried at 20°/0.1 mm over phosphorus pentoxide to give 205.9 g of 3-[8-[4-(2,2-diphenylethenyl)-1-piperidinyl]octyl]pyridine as a pale tan solid, mp 53°-54°. Liquid chromatography analysis indicated this material to be homogeneous.

EXAMPLE 43

Preparation of 3-[8-[4-(2,2-diphenylethenyl)-1-piperidinyl]octyl]pyridine (E)-2-butenedioate Salt A 2-L Erlenmeyer flask was charged with 205.5 g of 3-[8-[4-(2,2-diphenylethenyl)-1-piperidinyl]octyl]pyridine 420 mL of 2B ethanol, and 55.5 g (5% excess) of fumaric acid. The mixture was heated on a steam cone to solution and filtered through Celite into a 12-L flask equipped with a mechanical stirrer. The filter cake was washed with an additional 420 mL of warm 2B ethanol. The stirred filtrate was diluted rapidly with 5.10 L of acetone. Crystallization began within a few minutes. The suspension was cooled in an ice-acetone bath for 1.0 hour and filtered. The solid was washed with 2×1.0 L=2.0 L of cold acetone and dried in a forced air oven at 75° to give 249.9 g (97% yield) of 3-[8-[4-(2,2-diphenylethenyl)-1-piperidinyl]octyl]pyridine (E)-2-butenedioate salt as a white solid, mp 126°-127°. Lc showed this material to be homogeneous.

EXAMPLE 44

Preparation of alpha,alpha-Bis(3-methoxyphenyl)-4-pyridineethanol

To a stirred solution of 4-picoline (32,5 g) in tetrahydrofuran (140 ml), was added dropwise under argon a solution of phenyl lithium in 7:3 cyclohexane-ether (1.9M; 184 ml) at such a rate that the reaction temperature could be maintained at 10°-20° by means of an external cooling bath. After the addition was completed, the reaction was cooled to −5°, and then a solution of 3,3'-dimethoxybenzophenone (77.4 g) in dry tetrahydrofuran (140 ml) was added so that the reaction temperature did not exceed 0°. The cooling bath was removed and the mixture was stirred at room temperature for two hours, whereupon water (140 ml) was added slowly followed by tetrahydrofuran (140 ml). The layers were separated, and after sodium chloride (~30 g) was added to the aqueous phase, it was reextracted with tetrahydrofuran (2×100 ml). The combined organic layers were washed with brine (50 ml), then were dried (over sodium sulfate) and evaporated. The crude product was triturated with hot hexane (2×300 ml) and the resulting solid was filtered to give 93.5 g of alpha,alpha-bis(3-methoxyphenyl)-4-pyridineethanol, mp 134°-135°.

EXAMPLE 45

Preparation of alpha,alpha-Bis(3-methoxyphenyl)-4-piperidineethanol

A solution of alpha,alpha-bis(3-methoxyphenyl)-4-pyridine-ethanol (63 g) in acetic acid (400 ml) was hydrogenated over platinum oxide (2 g; 100 p.s.i.; 50°).

The reaction was stopped after the uptake of the theoretical amount of hydrogen (0.564 mol), then it was filtered to remove the catalyst and the solvent was evaporated under reduced pressure. After the residue was taken up in water (400 ml) and toluene (200 ml), the mixture was heated to reflux and then made basic with 10N sodium hydroxide. The mixture was cooled to 5°, and the resulting solid was collected by filtration, then was washed in turn with water, toluene, toluene-hexane (1:1) and hexane to give, after drying, 62.5 g of alpha,alpha-bis(3-methoxyphenyl)-4-piperidineethanol, mp 111°–113°.

EXAMPLE 46

Preparation of 4-[2,2-Bis(3-methoxyphenyl)ethenyl]piperidine

A solution of alpha,alpha-bis(3-methoxyphenyl)-4-piperidine-ethanol (15 g) in trifluoroacetic acid (30 ml) was stirred at ambient temperature for one hour, then the solvent was removed in vacuo. The residue was partitioned between toluene (50 ml) and 1N sodium hydroxide (100 ml), and the separated aqueous layer was reextracted with toluene (20 ml). The combined toluene extracts were washed with 1N sodium hydroxide solution, then were dried over potassium carbonate and evaporated to give 12.8 g of 4-[2,2-bis(3-methoxyphenyl)ethenyl]piperidine as an oil.

The above material was characterized as its hydrobromide salt, mp 135.5°–137°.

EXAMPLE 47

Preparation of 3-[8-[4-[2,2-Bis(3-methoxyphenyl)ethenyl]-1-piperidinyl]octyl]pyridine and its (1:1) ethanedioate 0.25 molar hydrated salt A mixture of 4-[2,2-bis(3-methoxyphenyl)ethenyl]-piperidine (1.65 g), 3-(8-chloroctyl)pyridine (1.13 g), sodium iodide (0.75 g) and anhydrous sodium carbonate (0.53 g) in dimethylformamide (10 ml) was stirred under argon at 75° for 16 hours. The solvent was removed in vacuo and the residue was taken up in a mixture of ethyl acetate and 1N sodium hydroxide solution. The separated aqueous layer was reextracted with three portions of ethyl acetate. The organic layers were washed in turn with water and brine, then were combined, dried over sodium sulfate, decolorized with charcoal and evaporated to give 2.5 g of crude product as an oil. The oil was purified by HPLC (hexane:ethyl acetate:triethylamine; 34:17:1) to give 1.8 g of 3-[8-[4-[2,2-bis(3-methoxyphenyl)ethenyl]-1-piperidinyl]octyl]pyridine, as an oil.

A solution of the above free base (1.7 g) in ethanol was treated with oxalic acid dihydrate (418 mg), then it was heated to reflux to dissolve the solids, filtered and diluted with ether (30 ml). The mixture was cooled and the resulting solid was filtered to give 2.0 g of 3-[8-[4-[2,2-bis(3-methoxyphenyl)ethenyl]-1-piperidinyl]octyl]pyridine (1:1) ethanedioate salt, 0.25 molar hydrate, mp 112°–115°. Recrystallization from ethanol-ether gave 1.5 g of product, mp 112°–115°. Analysis Calculated for $C_{34}H_{44}N_2O_2—C_2H_2O_4.0.25H_2O$: C, 71.20; H, 7.72; N, 4.61; $H_2O$, 0.74. Found: C, 71.22; H, 7.58; N, 4.58; $H_2O$, 0.58.

EXAMPLE 48

| TABLE FORMULATION | | |
|---|---|---|
| | mg/tablet | |
| Item | Ingredient | 250 mg | 500 mg |
| 1. | 3-[8-[4-(2,2-diphenyl-ethenyl)-1-piperidinyl]-octyl]pyridine | 250 | 500 |
| 2. | Lactose | 100 | 200 |
| 3. | Polyvinylpyrrolidone | 10 | 20 |
| 4. | Modified Starch | 10 | 20 |
| 5. | Magnesium Stearate | 3 | 6 |
| | | 373 mg | 746 mg |

1 Mix Items 1, 2 and 4 and granulate with polyvinylpyrrolidone in water or alcohol.
2 Dry the granulation at 45° C.
3 Mill the dried granulation through a suitable mill.
4 Add Item 5 and mix for three minutes and compress on a suitable press.

EXAMPLE 49

| TABLE FORMULATION (Wet Granulation) | | |
|---|---|---|
| | mg/tablet | |
| Item | Ingredient | 250 mg | 500 mg |
| 1. | 3-[8-[4-(2,2-diphenyl-ethenyl)-1-piperidinyl]-octyl]pyridine | 250 | 500 |
| 2. | Lactose | 75 | 150 |
| 3. | Pregelatinized Starch | 15 | 30 |
| 4. | Microcrystalline Cellulose | 75 | 150 |
| 5. | Magnesium Stearate | 3 | 6 |
| | | 418 mg | 836 mg |

1 Mix Items 1, 2, 3 and 4 and granulate with water.
2 Dry the granulation at 50° C.
3 Pass the granulation through suitable milling equipment.
4 Add Item 5 and mix for three minutes; compress on a suitable press.

EXAMPLE 50

| CAPSULE FORMULATION | | |
|---|---|---|
| | mg/capsule | |
| Item | Ingredient | 250 mg | 500 mg |
| 1. | 3-[8-[4-(2,2-diphenyl-ethenyl)-1-piperidinyl]-octyl]pyridine | 250 | 500 |
| 2. | Corn Starch (Pregelatinized) | 20 | 40 |
| 3. | Modified Starch | 10 | 20 |
| 4. | Talc | 10 | 20 |
| 5. | Magnesium Stearate | 1 | 2 |
| | | 291 mg | 582 mg |

1 Mix Items 1, 2 and 3 and wet granulate with water. Dry at 45° C. overnight.
2 Mill through suitable screen using appropriate milling equipment.
3 Add Items 4 and 5 and mix for five minutes.
4 Fill into suitable capsule.

We claim:
1. A compound of the formula

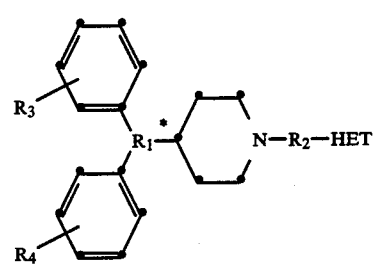

I wherein $R_1$ is

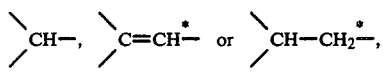

the asterisk denotes the bonding orientation to the piperidine moiety; $R_2$ is alkylene or $-CO-(CH_2)_n-$ wherein n is 0 to 11; $R_3$ and $R_4$, independently, are hydrogen, halogen or lower alkoxy; and HET is pyridinyl, pyrimidinyl or imidazolyl, or a salt thereof with a pharmaceutically acceptable acid.

2. A compound, in accordance with claim 1, wherein $R_2$ is alkylene.

3. A compound, in accordance with claim 1, wherein $R_2$ is $-CO-(CH_2)_n-$.

4. A compound, in accordance with claim 2, wherein $R_1$ is

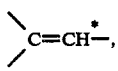

$R_2$ is alkylene of 1 to 12 carbon atoms, $R_3$ is hydrogen and HET is pyridinyl or pyrimidinyl.

5. A compound, in accordance with claim 2, wherein $R_1$ is

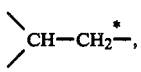

$R_2$ is alkylene of 1 to 12 carbon atoms, $R_3$ is hydrogen and HET is pyridinyl or pyrimidinyl.

6. A compound, in accordance with claim 4, wherein $R_1$ is

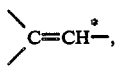

$R_2$ is alkylene of 4 to 10 carbon atoms, $R_3$ is hydrogen and HET is pyridinyl.

7. A compound, in accordance with claim 5, wherein $R_1$ is

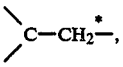

$R_2$ is alkylene of 4 to 10 carbon atoms, $R_3$ is hydrogen and HET is pyridinyl.

8. A compound, in accordance with claim 1, 3-[8-[4-(2,2-diphenylethenyl)-1-piperidinyl]octyl]pyridine.

9. A compound, in accordance with claim 1, 3-[7-(4-(2,2-diphenylethenyl)-1-piperidinyl]heptyl]pyridine (1:1)-(E)-2-butenedioate salt hemihydrate.

10. A compound, in accordance with claim 1, 3-[6-[4-(2,2-diphenylethenyl)-1-piperidinyl]hexyl]pyridine (1:1)-(E)-2-butenedioate salt.

11. A compound, in accordance with claim 1, 3-[5-[4-(2,2-diphenylethenyl)-1-piperidinyl]pentyl]pyridine (1:1)-(E)-2-butenedioate salt.

12. A pharmaceutical composition for treating obesity and for lowering insulin activity comprising a compound of the formula

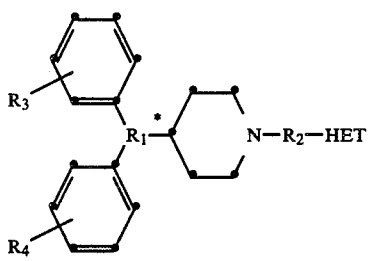

wherein $R_1$ is

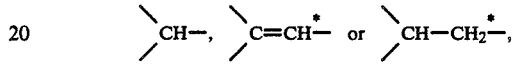

the asterisk denotes the bonding orientation to the piperidine moiety; $R_2$ is alkylene or $-CO-(CH_2)_n-$ wherein n is 0 to 11; $R_3$ and $R_4$, independently, are hydrogen, halogen or lower alkoxy; and HET is pyridinyl, pyrimidinyl or imidazolyl, or a salt thereof with a pharmaceutically acceptable acid, and an inert pharmaceutical carrier material.

13. A pharmaceutical composition, in accordance with claim 12, wherein $R_1$ is

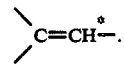

14. A pharmaceutical composition, in accordance with claim 12, wherein the compound of formula I is 3-[8-[4-(2,2-diphenylethenyl)-1-piperidinyl]octyl]pyridine.

15. A method of treating obesity which comprises administering to a host requiring such treatment an effective amount of a compound of the formula

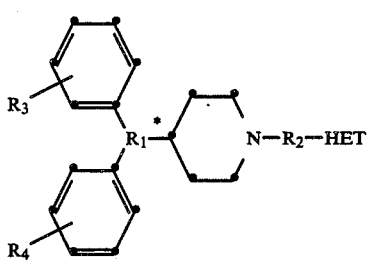

wherein $R_1$ is

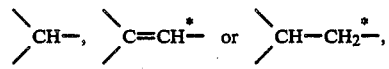

the asterisk denotes the bonding orientation to the piperidine moiety; $R_2$ is alkylene or $-CO-(CH_2)_n-$ wherein n is 0 to 11; $R_3$ and $R_4$, independently, are hydrogen, halogen or lower alkoxy; and HET is pyridinyl, pyrimidinyl or imidazolyl, or a salt thereof with a pharmaceutically acceptable acid.

16. A method, in accordance with claim 15, wherein $R_1$ is

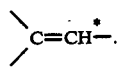

17. A method, in accordance with claim 15, wherein the compound of formula I is 3-[8-[4-(2,2-diphenylethenyl)-1-piperidinyl]octyl]pyridine.

18. A compound, in accordance with claim 1, 3-[10-[4-(2,2-diphenylethenyl)-1-piperidinyl]decyl]pyridine.

19. A pharmaceutical composition, in accordance with claim 12, wherein the compound of formula I is 3-[10-[4-(2,2-diphenylethenyl)-1-piperidinyl]decyl]pyridine.

20. A method, in accordance with claim 15, wherein the compound of formula I is 3-[10-[4-(2,2-diphenylethenyl)-1-piperidinyl]decyl]pyridine.

* * * * *